(12) United States Patent
Moscovitch

(10) Patent No.: US 9,151,715 B2
(45) Date of Patent: Oct. 6, 2015

(54) DOSIMETRY SYSTEM BASED ON OPTICALLY STIMULATED LUMINESENCE

(75) Inventor: Marko Moscovitch, Chevy Chase, MD (US)

(73) Assignee: Georgetown University, Washington, DC (US)

( * ) Notice: Subject to any disclaimer, the term of this patent is extended or adjusted under 35 U.S.C. 154(b) by 331 days.

(21) Appl. No.: 13/574,227

(22) PCT Filed: Jan. 25, 2011

(86) PCT No.: PCT/US2011/022465
§ 371 (c)(1),
(2), (4) Date: Jul. 19, 2012

(87) PCT Pub. No.: WO2011/094234
PCT Pub. Date: Aug. 4, 2011

(65) Prior Publication Data
US 2012/0292532 A1 Nov. 22, 2012

Related U.S. Application Data

(60) Provisional application No. 61/298,493, filed on Jan. 26, 2010.

(51) Int. Cl.
*G01T 1/11* (2006.01)
*G01N 21/64* (2006.01)

(52) U.S. Cl.
CPC ........ *G01N 21/6486* (2013.01); *G01N 21/6408* (2013.01); *G01T 1/11* (2013.01); *G01N 2021/6419* (2013.01); *G01N 2201/0221* (2013.01)

(58) Field of Classification Search
CPC .......... G01N 21/6486; G01N 21/6428; G01N 21/6408; G01N 21/64; G01N 2201/0221; G01T 1/10; G01T 1/11; A61B 5/00; A61B 2017/00057
See application file for complete search history.

(56) References Cited

U.S. PATENT DOCUMENTS

| | | | | | |
|---|---|---|---|---|---|
| 4,894,547 | A | * | 1/1990 | Leffell et al. | 250/461.2 |
| 5,136,163 | A | * | 8/1992 | Miller et al. | 250/337 |
| 5,818,056 | A | | 10/1998 | Pass | |
| 5,892,234 | A | | 4/1999 | McKeever et al. | |
| 5,962,857 | A | * | 10/1999 | McKeever et al. | 250/484.5 |
| 6,936,830 | B2 | | 8/2005 | Gaza et al. | |
| 7,002,163 | B2 | | 2/2006 | Polf et al. | |
| 7,084,628 | B2 | * | 8/2006 | Swartz et al. | 324/316 |

(Continued)

FOREIGN PATENT DOCUMENTS

JP 2000-203396 3/2000

OTHER PUBLICATIONS

Alexander G.A. et ai., Biodos-EPR—2006 Meeting: Acute dosimetry consensus committee recommendations on biodosimetry applications in events involving uses of radiation by terrorists and radiation accidents. Radiation Measurements 42 (2007) 972-996.
Chandra et al., Sulfur radicals formed by cutting a-keratin. (1987) Nature 328:833-834.

(Continued)

*Primary Examiner* — Yara B Green
(74) *Attorney, Agent, or Firm* — Knobbe, Martens, Olson & Bear LLP

(57) ABSTRACT

Methods for detecting exposure to ionizing radiation are provided. In particular, methods for detecting and measuring the exposure of keratin-rich materials to ionizing radiation using optically stimulated luminescence are provided.

24 Claims, 4 Drawing Sheets

(56) References Cited

U.S. PATENT DOCUMENTS

| | | |
|---|---|---|
| 7,098,470 B2 | 8/2006 | Akselrod et al. |
| 2003/0078504 A1* | 4/2003 | Rowe ........................ 600/476 |
| 2004/0238757 A1 | 12/2004 | Gaza et al. |
| 2006/0088444 A1 | 4/2006 | Gambini et al. |
| 2007/0049996 A1* | 3/2007 | Black ........................ 607/89 |
| 2011/0191874 A1* | 8/2011 | Carlock et al. ............ 800/14 |
| 2012/0277555 A1* | 11/2012 | Paseman et al. .......... 600/317 |

OTHER PUBLICATIONS

Romanyukha A. et al., EPR dosimetry in chemically treated fingernails. Radiation Measurements (2007) 42: 1110-1113.

Trompier F. et al., Electron paramagnetic resonance radiation dosimetry in fingernails. Radiation Measurements (2009) 44:6-10.

Trompier F. et al., Protocol for emergency EPR dosimetry in fingernails. Radiation Measurements (2007) 42:1085-1088.

* cited by examiner

DOSIMETRY SYSTEM BASED ON OPTICALLY STIMULATED LUMINESENCE

CROSS-REFERENCE TO RELATED APPLICATIONS

This application is the national phase under 35 U.S.C. §371 of prior PCT International Application No. PCT/US2011/022465 which has an International Filing Date of Jan. 25, 2011, which designates the United States of America, and which claims priority to U.S. Provisional Application No. 61/298,493, filed Jan. 26, 2010, the disclosures of which are hereby expressly incorporated by reference in their entirety and are hereby expressly made a portion of this application.

FIELD OF THE INVENTION

Methods for detecting exposure to ionizing radiation are provided. In particular, methods for detecting and measuring the exposure of keratin-rich materials to ionizing radiation using optically stimulated luminescence are provided.

BACKGROUND OF THE INVENTION

Exposure to high levels of ionizing radiation can be harmful. Measuring the level of an individual's exposure can be useful in allocating resources and determining appropriate methods of treatment. In some circumstances, it can be useful to determine the exposure of an entire population to a source of ionizing radiation, for example, in mass-casualty radiation accidents, or in incidents of radiological terrorism (Alexander G. A. et al., Biodos-EPR-2006 Meeting: Acute dosimetry consensus committee recommendations on biodosimetry applications in events involving uses of radiation by terrorists and radiation accidents. Radiation Measurements 42 (2007) 972-996).

First responders and receivers (i.e. physicians and nurses) need guidance to perform triage based on dose assessment, so that those who are at risk of significant acute radiation effects are identified and entered into the health care system. For example, individuals with sub clinical exposures (for example, less than about 1.5 Gy) can be followed as outpatients. Individuals with significant absorbed doses (for example, in the range of about 1.5-10 Gy) can be referred to hospitals for treatment, while those with higher absorbed doses (for example, greater than about 10 Gy) may be triaged for compassionate care or to heroic measures, if resources are available. Dose assessments can contribute to medical treatment decisions.

Several techniques exist that are useful to estimate the level an individual may have been exposed to ionizing radiation. These include cytogenetic assays, electron spin resonance (ESR) or electron paramagnetic resonance (EPR), and luminescence techniques.

Cytogenetic assays measure the effects of ionizing radiation on the cells of an exposed individual. These assays include culturing cells from an individual, then visualizing chromosomal aberrations in such cells. Cytogenetic assays are therefore invasive, expensive, and time-consuming.

ESR detects free electrons produced in the tissues of an individual on exposure to high levels of ionizing radiation. Generally, ESR cannot be carried out in the presence of large amounts of water and had therefore been limited to relatively dry samples, such as extracted teeth. Recently, ESR has been applied to tissues such as fingernail and toenail parings (Romanyukha A. et al., EPR dosimetry in chemically treated fingernails. Radiation Measurements (2007) 42:1110-1113; Trompier F. et al., Protocol for emergency EPR dosimetry in fingernails. Radiation Measurements (2007) 42:1085-1088; and Trompier F. et al., Electron paramagnetic resonance radiation dosimetry in fingernails. Radiation Measurements (2009) 44:6-10).

SUMMARY OF THE INVENTION

In view of the above drawbacks of conventional methods for determining exposure to levels of ionizing radiation, the development of methods, devices and kits for detecting and measuring exposure to ionizing radiation that are non-invasive, rapid, cost effective and reliable is highly desirable.

Devices and kits for detecting exposure of a biological material to ionizing radiation are provided, e.g., for detecting and measuring exposure of a biological material to ionizing radiation using OSL. Methods can include exposing a material to an ultraviolet (UV) light source effective to stimulate luminescence in the material; and detecting emitted light from the material, whereby an increase in emitted light compared to an unexposed material may indicate exposure to ionizing radiation.

The material to be tested can comprise keratin, e.g., nail, hair, skin, carapace, claw, quill, beak, hoof, or feather. An in vivo sample or an ex vivo sample can be tested.

In some embodiments, the exposing and detecting steps are performed at about ambient temperature. In some such embodiments, ambient temperature is from about 15° C. to about 35° C.

In some embodiments, the UV light source has a wavelength of from about 200 nm to about 380 nm, e.g., a wavelength of about 300 nm or a wavelength of about 254 nm.

In some embodiments, the emitted light has a wavelength in the broadband visible range, e.g., from about 380 nm to about 750 nm, preferably from about 400 nm to about 600 nm.

The ionizing radiation can include UV light, x-ray rays, gamma rays, beta particles, neutrons, alpha particles, heavy ions or protons.

In addition to the foregoing methods, methods for determining a radiation parameter of a biological material, e.g., a keratin-comprising sample as discussed above, exposed to ionizing radiation are also provided. Such methods can include exposing a material to a UV light source effective to stimulate luminescence in the material, measuring emitted light from the material, comparing a value representative of the emitted light to a correction factor, and estimating the radiation parameter of the biological material exposed to ionizing radiation.

In some embodiments the radiation parameter can be a radiation cumulative dose, a radiation dose rate, an instantaneous radiation dose rate, an amount of radiation energy deposited in the material, or a rate of energy deposition in the material.

In addition to the foregoing methods, devices are also provided for detecting exposure of a biological material to ionizing radiation. Such devices can include a UV light adapted to stimulate luminescence in a biological sample, a detector adapted to detect emitted light from the biological sample, and a chamber or orifice adapted to receive the biological sample. Devices may further include a central processing unit and memory. The chamber can be adapted for receiving an ex vivo biological sample, and/or adapted for receiving an in vivo biological sample. In some embodiments, devices can be adapted to operate at ambient temperature. In some embodiments, devices are portable and/or hand-held.

In addition to the foregoing methods and devices, kits are also provided for detecting exposure of a biological material to ionizing radiation. The kits can include any device described herein, and instructions for use thereof. In some embodiments, kits may further comprise tools for obtaining a biological sample.

DETAILED DESCRIPTION

Figure 1:
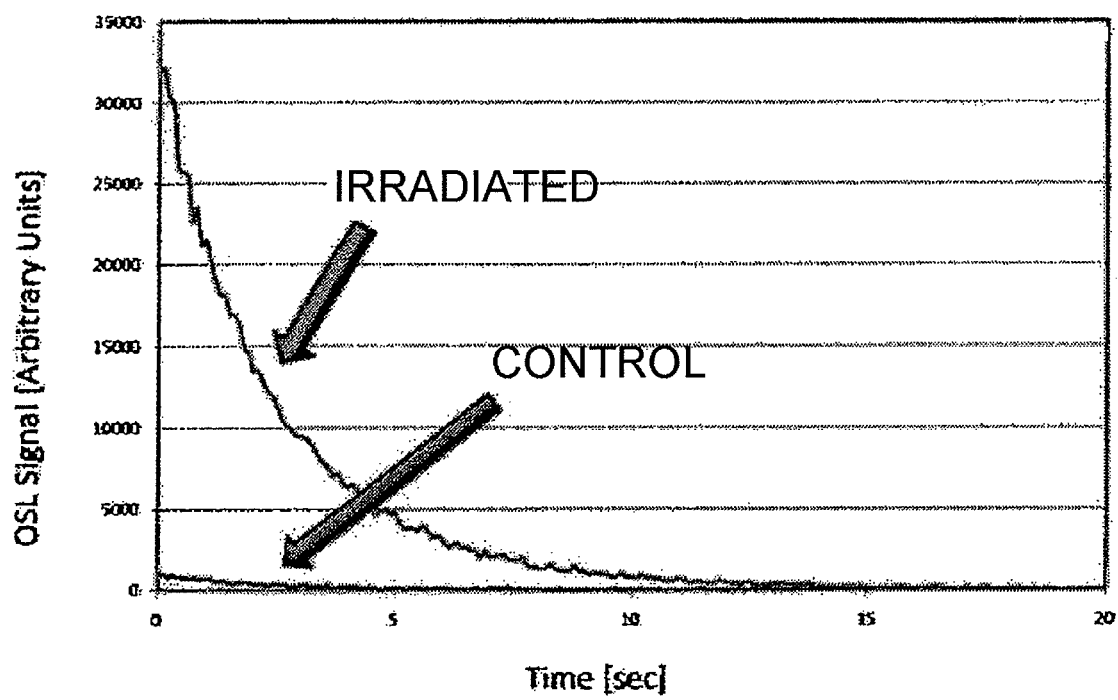
FIG. 1 shows a graph of OSL emitted light over time from irradiated fingernail parings, and a control of non-irradiated fingernail parings.

The following description and examples illustrate a preferred embodiment of the present invention in detail. Those of skill in the art will recognize that there are numerous variations and modifications of this invention that are encompassed by its scope. Accordingly, the description of a preferred embodiment should not be deemed to limit the scope of the present invention.

Methods, devices, and kits useful for detecting exposure of biological materials to ionizing radiation using optically stimulated luminescence (OSL). The term "ionizing radiation" as used herein is a broad term, and is to be given its ordinary and customary meaning to a person of ordinary skill in the art (and is not to be limited to a special or customized meaning), and refers without limitation to subatomic particles and electromagnetic such as UV light, x-ray rays, gamma rays, beta particles, alpha particles, and protons. Some methods include exposing a biological material to a UV light source effective to stimulate luminescence in the material; and detecting emitted light from the material.

Radiation-induced stimulatable luminescence of a wide variety of natural and manufactured materials has been studied since the early decades of the 20th century. Initial research focused on the chronology and authentication of archaeological objects. Such methodologies may be suitable for the detection of very low absorbed doses of radiation. In these techniques, luminescence is stimulated either thermally as in thermoluminescence (TL) or optically (OSL). Infrared or visible light is often used in OSL. One technique involves the application of OSL to irradiated teeth for the purpose of dose estimation. This approach often requires tooth extraction or insertion of a probe needs into the mouth of the potentially exposed patient. Exposure of samples to visible light prior to OSL may limit accuracy of measurements.

ESR has been applied to tissues such as fingernail and toenail parings, as discussed above. In some implementations, ESR may require large magnets, thus limiting its use in the field. ESR equipment is generally expensive to purchase and costly to maintain. The sensitivity and accuracy of ESR may be limited and the dose information may be retained for only a few hours post exposure. ESR may require additional sample preparation steps such as water or chemical treatment and the intensity of the ESR signal is often highly dependant on environmental conditions such as temperature and humidity.

Particular applications of optically stimulated luminescence (OSL) to radiation dosimetry using fingernails or toenails may be implemented to realize one or more of the following advantages. The radiation dosimetry method and/or device disclosed herein may provide a simple, cost effective, and accurate measurement of an individual's radiation exposure. Determining a level of irradiation by stimulating finger nails with UV light at ambient temperature and measuring the luminescence emitted from the nails may provide a method and/or device capable of triaging a large population quickly and effectively.

OSL is a technique that can be used to determine the level of absorbed radiation dose in materials. Typically, the material is stimulated with low energy visible or infrared photons. Absorption of visible photons leads to ejection of the charges into the conduction band. Subsequently, luminescence is emitted as a result of recombination of the de-trapped charges with holes in the band gap. The number of photons emitted by the substance is proportional to the radiation dose absorbed at some earlier time (see, e.g., U.S. Pat. Nos. 5,818,056, 5,892,234, 6,936,830, 7,002,163, and 7,098,470, the text of each of which is incorporated by reference herein in its entirety). Radiation dependent and time dependent OSL signals may be obtained and used for retrospective dosimetry on the materials. OSL signals may also be integrated over a time period and used to determine an unknown absorbed dose.

The instant disclosure demonstrates that an OSL emitted light signal can be induced in irradiated biological materials using UV light (photons). Such an OSL emitted light signal can therefore indicate exposure of the biological material to ionizing radiation. Radiation parameters, such as absorbed dose, can also be determined from the OSL of the biological sample.

Biological samples can include keratin-rich samples. Accordingly, one advantage of the methods described herein therefore includes the use of fingernail and toenail parings as biological materials for use in the methods, devices, and kits described herein. As will be appreciated, such samples are readily available, and can be easily obtained from large numbers of individuals.

In addition, it has also been discovered that some of the methods described herein can be performed at ambient temperature. Consequently, such methods can be performed in the field, and may also be performed in vivo. The following describes biological materials that can be used with the methods, devices, and kits described herein.

Biological Materials

Some methods include the use of biological materials that can be induced to undergo OSL. The term "keratin" as used herein is a broad term, and is to be given its ordinary and customary meaning to a person of ordinary skill in the art (and is not to be limited to a special or customized meaning), and refers without limitation to any of a family of scleroproteins that are principal constituents of epidermis, hair, nails, horny tissues, and the organic matrix of tooth enamel. In some embodiments, keratin-rich materials can be used in accordance with the methods described herein. Keratin-rich materials can be obtained from humans and other animals such as other mammals, marsupials, reptiles, amphibians, and birds. Examples of keratin-rich materials are well known and include tissues such as fingernails, toenails, hair and skin. More examples include horns, hooves, claws, beaks, feathers, quills, scales, and shells, and wool.

As will be understood, other biological materials which can be induced to undergo OSL can be used with the methods described herein. Such materials can include proteinaeous materials or matrices, e.g., those comprising proteins such as silk or chitin. Such materials may also include organic polymers such as cellulose or lignin.

Samples of biological materials can be utilized with the methods described herein ex vivo. In such embodiments, a biological material is removed from an individual. For example, fingernail, toenail or hair, is cut from an individual. In other embodiments, samples of biological materials are utilized in vivo. In some such embodiments, the biological sample remains an integral part of an individual.

Advantages of some methods described herein include the ability to assess exposure to different parts of an individual's body. Thus, in some such embodiments, a plurality of samples from different locations are taken from a single individual. For example, fingernail and toenail parings are taken and used to assess the differences in exposure of different parts of an individual's body.

In some embodiments, ex vivo samples are utilized immediately after removal of the material from an individual. As will be understood, the material can be used at any time after removing the sample from an individual. In some embodiments, the material is stored to preserve a signal, for example, the sample can be stored at lower temperatures, e.g., less than 0° C., such as at −4° C., or −20° C.

Detecting Exposure

Some methods for detecting exposure of a biological material to ionizing radiation include exposing the material to a light source effective to stimulate luminescence in the material, and detecting the emitted light from the material. The ionizing radiation can include UV light, x-ray rays, gamma rays, beta particles, neutrons, alpha particles, heavy ions or protons. Exposing a biological material to a stimulating light source effective to stimulate luminescence in the material can include placing an irradiated material in the path of a stimulating light source, where the light source has sufficient intensity and appropriate wavelength to stimulate luminescence in the irradiated material.

One or more steps of the methods of preferred embodiments can be performed at any suitable temperature, either with or without applied heating or cooling. In some embodiments, one or more steps can be performed at ambient temperature. The term "ambient temperature" as used herein is a broad term, and is to be given its ordinary and customary meaning to a person of ordinary skill in the art (and is not to be limited to a special or customized meaning), and refers without limitation to and can include a temperature characteristic of a lack of applied heating or cooling of a biological material during one or more steps in methods for detecting exposure of the material to ionizing radiation. For example, in some embodiments, where one or more steps are performed ex vivo, ambient temperature can include room temperature (e.g., 20° C. to 25° C.) at which the methods are performed. In some embodiments, where one or more steps are performed in vivo, ambient temperature can include temperatures from about room temperature at which the methods are performed and the temperature of the biological material associated with an individual, for example, the body temperature of the individual, or the temperature of the biological material attached to the individual. In some embodiments, ambient temperature is from about 5° C. to about 45° C., preferably from about 10° C. to about 40° C., more preferably from about 15° C. to about 35° C., and most preferably from about 20° C. to about 30° C.

Stimulating Light Sources

Stimulating light sources that are suitable for use with the devices and methods of preferred embodiments include UV light sources. Sources of UV light can include, for example, fluorescent lamps, discharge lamps, incandescent lamps, and light emitting diodes. The UV light source may include a laser of sufficient power. In some embodiments, the UV light source emits multiple wavelengths. In other embodiments, UV light source emits a single wavelength. In some embodiments, fiber optics may be employed to transmit the stimulating light from the light source.

The wavelength of the UV light can be from about 10 nm to about 400 nm, preferably from about 100 nm to about 380 nm, more preferably from about 200 nm to about 350 nm, or most preferably from about 230 nm to about 320 nm. In some embodiments, the UV light has a wavelength of from about 10 nm to about 400 nm and a peak emission at about 300 nm or about 254 nm, more preferably a wavelength of from about 100 nm to about 380 nm and a peak emission at about 300 nm or about 254 nm, even more preferably a wavelength of from about 200 nm to about 350 nm and a peak emission at about 300 nm or about 254 nm, and most preferably a wavelength of from about 230 nm to about 320 nm and a peak emission at about 300 nm or about 254 nm. In some embodiments, the UV light has a peak emission at and a wavelength of about 300 nm. In some embodiments, the UV light has a peak emission at and a wavelength of about 254 nm.

In some embodiments, the stimulating light may utilize a combination of wavelengths. For example, the irradiated sample may be stimulated by a first wavelength and the luminescence may be read. Subsequently, the sample may stimulated by a second wavelength and a second luminescence may be read. In some embodiments, the stimulating light may also include more than one wavelength or a range or wavelengths.

The biological material can be exposed to a pulsed or continuous UV light. Pulsed exposures of UV light can have pulse widths of from about 1 ns to about 500 ms; however, longer or shorter pulse widths can be suitable in certain embodiments. The pulses can be regular in frequency, irregular in frequency, and/or intermittent. The period that the biological material is exposed to UV light is typically from about 1 ns to 5 minutes; however, longer or shorter exposure times can also be employed in certain embodiments. In some embodiments, the period that the biological material is exposed to UV light is from about 1 seconds to about 600 seconds, preferably from about 1 seconds to about 300 seconds, more preferably from about 1 seconds to about 100 seconds, still more preferably from about 1 seconds to about 60 seconds, more preferably still from about 1 seconds to about 30 seconds, and most preferably from about 1 seconds to about 10 seconds.

Detecting OSL

Stimulating and detecting steps can be performed sequentially or concurrently. For example, in some embodiments, detecting the emitted light is performed subsequent to exposing the material to the stimulating light source. In other embodiments, detecting emitted light is performed while the material is exposed to the stimulating light source. Filters can be used to discriminate between stimulating light sources and emitted light sources.

OSL from a biological material can include emitted light in the visible light spectrum. Some methods described herein include detecting emitted light with a wavelength of from about 300 nm to about 800 nm, more preferably from about 380 nm to about 750 nm. The luminescence emission can include various wavelengths in the range from about 380 nm to about 750 nm.

OSL emitted light can be collected by a detector for an acquisition time that varies from a fraction of a second to several minutes or more. In some embodiments, OSL emitted light is collected by a detector for an acquisition time greater than about 100 ms, about 200 ms, about 300 ms, about 400 ms, about 500 ms, or about 1000 ms. In some embodiments, OSL emitted light is collected by a detector for an acquisition time greater than about 1 second, about 5 seconds, about 10 seconds, about 20 seconds, about 30 seconds, about 60 seconds, about 100 seconds, about 200 seconds, about 500 seconds, or about 1000 seconds. OSL emitted light signal is detected as a peak emission or as a cumulative signal over a period of time, such as the period of the acquisition time. In addition, the detected OSL emitted light signal can be detected as an integrated value.

Detectors suitable for detecting OSL, including OSL wherein emitted light is in the visible spectrum, include, for example, colorimeters, fiber optic sensors, photodiodes, phototransistors, photocells, photoelectric sensors, photoionization detectors, photomultiplier tubes, photoresistors, photoswitches, phototubes, photovoltaic cells, and wavefront sensors. In some embodiments, fiber optics may be employed to receive and transmit the luminescence.

Detecting a signal of OSL emitted light from a biological material greater than an unexposed sample of a biological material is indicative that a biological material has been exposed to ionizing radiation. Some embodiments include measuring the level of OSL, for example, measuring the intensity and/or duration of emitted light from a biological sample to estimate the absorbed dose that the biological had received.

Estimating Absorbed Dose

Some methods described herein include estimating the absorbed dose of ionizing radiation a biological material has received. The absorbed dose, also known as total ionizing dose, is a measure of the energy deposited in a medium by ionizing radiation and is often defined as the energy deposited per unit mass of medium. The SI unit of absorbed dose is the Gray (Gy).

OSL emitted light signal is correlated to the absorbed dose to a biological material, such as a keratin-rich material. In some embodiments, in order to correlate an OSL emitted light signal with absorbed radiation dose, dose-response curves or relational data, namely calibration curves, are experimentally established over the range of absorbed dose to be monitored, such as from about 1 cGy to about 100 Gy. The curves or data can be established for a variety of different factors. For example, it is known that different ionizing radiation sources have different effects on biological materials; therefore the effects of different ionizing radiation sources on OSL signal can be determined. The effects of time between exposure and detecting and measuring an OSL signal can also be determined. In addition, the effects of ionizing radiation on different biological materials, such as fingernail and toenail parings can be determined. Therefore, in some embodiments, OSL emitted light signal can be correlated to an absorbed dose using calibration curves. In some embodiments, the calibration curves are predetermined.

In addition to absorbed dose, OSL emitted signal from a biological material can be used to estimate an effective dose. The absorbed dose is not necessarily a good indicator of the likely biological effect of radiation exposure. For example, one Gray of alpha radiation is likely much more biologically damaging than one Gray of photon radiation. As such, appropriate weighting factors can be applied reflecting the different relative biological effects to find the equivalent dose. The effective dose can also be used to compare radiation doses on different body parts on an equivalent basis because radiation does not affect different parts of an individual's body in the same way. The effective dose to a given individual can be found by calculating a weighted average of the equivalent dose to different body tissues, with weighting factors designed to reflect the different radiosensitivities of the tissues. The SI unit of effective dose is the Sievert (Sv).

Additional radiation parameters associated with the exposure of a biological material to ionizing radiation can be estimated. As described herein, calibration curves can be determined and used to estimate radiation parameters, such as, radiation cumulative dose, radiation dose rate, instantaneous radiation dose rate, amount of radiation energy deposited in the material, and a rate of energy deposition in the biological material (see, e.g., U.S. Pat. Nos. 7,002,163 and 6,936,830, the disclosures of which are incorporated by reference herein in their entireties).

Data and calibration curves described herein can be used to provide correction factors with which to compare an OSL emitted light signal in order to estimate a radiation parameter for a biological material exposed to ionizing radiation. Correction factors can account for variables that affect an OSL emitted signal, for example, the period of time after exposure to ionizing radiation of a biological material, type of ionizing radiation, water content of the biological material, and OSL emitted signal induced by a biological material exposed to chemical, mechanical and disease states. For example, mechanical stress may cause the formation of sulfur radicals in keratin-rich materials that may give rise to a background signal (Chandra et al., Sulfur radicals formed by cutting a-keratin. (1987) Nature 328:833-834, incorporated by reference in its entirety). Such backgrounds signals may be removed by appropriate data processing, often because the mechanical induced signal has a different shaped response than the radiation induced signal.

Devices

Devices for detecting the exposure of a biological material to ionizing radiation are provided. Such devices can include a stimulating light adapted to stimulate an OSL signal in a biological sample, and a detector adapted to detect an OSL from a biological sample. In certain embodiments, the device can include a UV light source adapted to stimulate OSL in a biological material, and a detector adapted to detect OSL in a biological material. Devices can be adapted for exposing a biological sample to a stimulating light source and/or adapted for detecting OSL from the biological sample ex vivo. Such devices can include a chamber, and/or orifice for receiving the ex vivo biological sample. Devices can be adapted for exposing a biological sample to a stimulating light source and/or adapted for detecting OSL from the biological sample in vivo. Such devices can include a chamber, and/or orifice for receiving the in vivo biological sample. Sample-to-detector geometry may be optimized to increase resolution.

Some devices of preferred embodiments further include a central processing unit useful for comparing an OSL emitted light signal with data and/or calibration curves to calculate a radiation parameter. Such devices may further include a memory. Some embodiments may incorporate a display which may be coupled to a central processing unit to display data.

Device electronics may accomplish the detection and counting of photons, calibration of the luminescence signal, and generation of a radiation dose output. The device may include controls for adjusting the optical source to provide a predetermined exposure of optical photons and controls for adjusting the detector to detect the intensity of OSL over a predetermined interval. Data representing the dose-response curve using correlative exposure and detection parameters can be obtained and stored in electronic format in memory. Such curves and/or parameters can be used to directly correlate the measured response to absorbed radiation dose. In some embodiments, an appropriate calibration algorithm can be established, stored, and used to convert the detected luminescence response to radiation dose.

Some devices can be adapted to be operated at ambient temperature. Devices can further have a unitary design, be portable, or be handheld.

Kits

Kits for detecting the exposure of a biological material to ionizing radiation are provided. Such kits may include devices described herein further comprising instructions for use thereof, or include tools for obtaining a biological material, for example, scissors, or a knife.

EXAMPLE 1

Freshly-cut fingernail parings were irradiated with approximately 40 Gy from a $^{137}$Cs γ-ray source. The irradiated fingernail parings were exposed to a UV light source (λ=254 nm) for a short period (about 3 seconds), and then immediately placed on the reader planchet of a TLD reader (Harshaw Model 3500). The TLD reader was operated at ambient temperature by selecting a time-temperature-profile where the maximum temperature was room temperature (approximately 25° C.). The acquisition time was set to 20 seconds, and the photomultiplier tube of the TLD reader was used to collect the light emitted by the fingernail. Non-irradiated fingernail parings were used as a control.

As shown in FIG. 1, the irradiated fingernail provided an initial OSL signal at least about 20 times greater than the non-irradiated control, indicating significant OSL effects in fingernails. In addition, since the readout process does not involve heating, a fingernail can be measured in vivo. Furthermore, the OSL readout can be done multiple times without destroying the information. This kind of OSL process is called "delayed OSL" since the OSL light is collected after the stimulation ends. Thus, irradiated fingernails may exhibit OSL properties.

EXAMPLE 2

Figure 2:
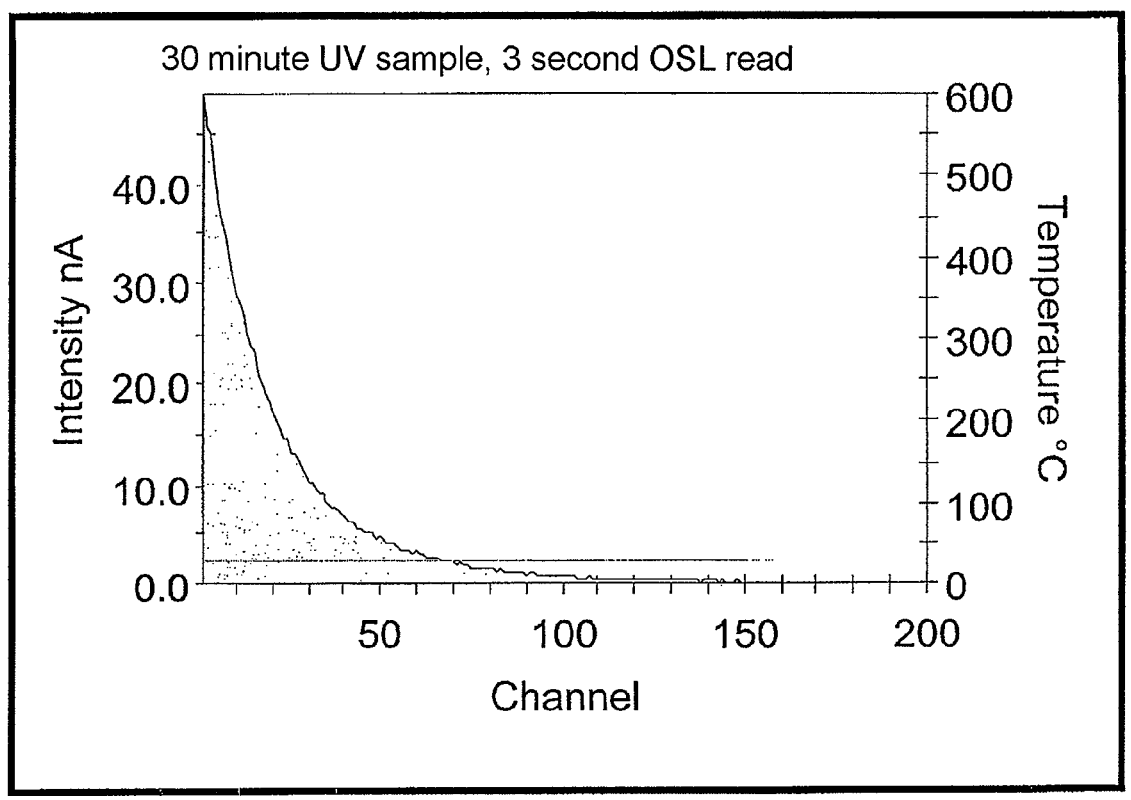
FIG. 2 shows a graph of OSL emitted light over time from irradiated fingernail parings.
Figure 3:
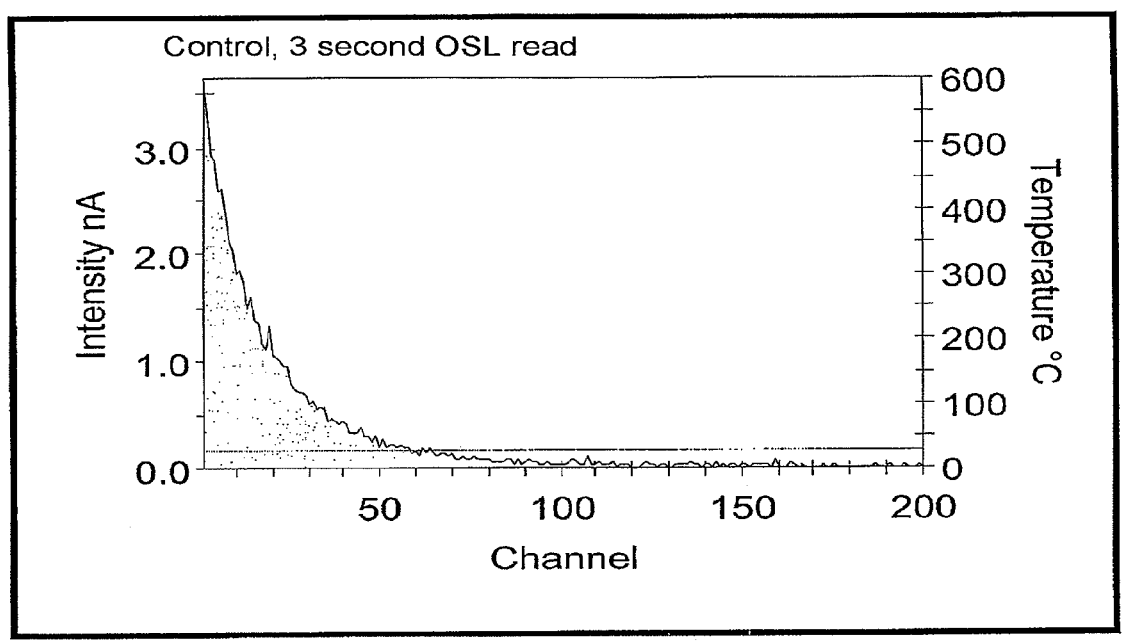
FIG. 3 shows a graph of OSL emitted light over time from a control of non-irradiated fingernail parings.

Fingernails were irradiated for 30 minutes with a UV light source (λ=300 nm), and then read using a 3 second pulse from a UV light source (the same UV source). The OSL signal was detected and measured for 20 seconds. A control experiment included fingernails not irradiated for 30 minutes to the UV light source (λ=300 nm). As shown in FIG. 2 and FIG. 3, the initial OSL signal of the irradiated sample was at least about 20 times higher than the control.

EXAMPLE 3

Figure 4:
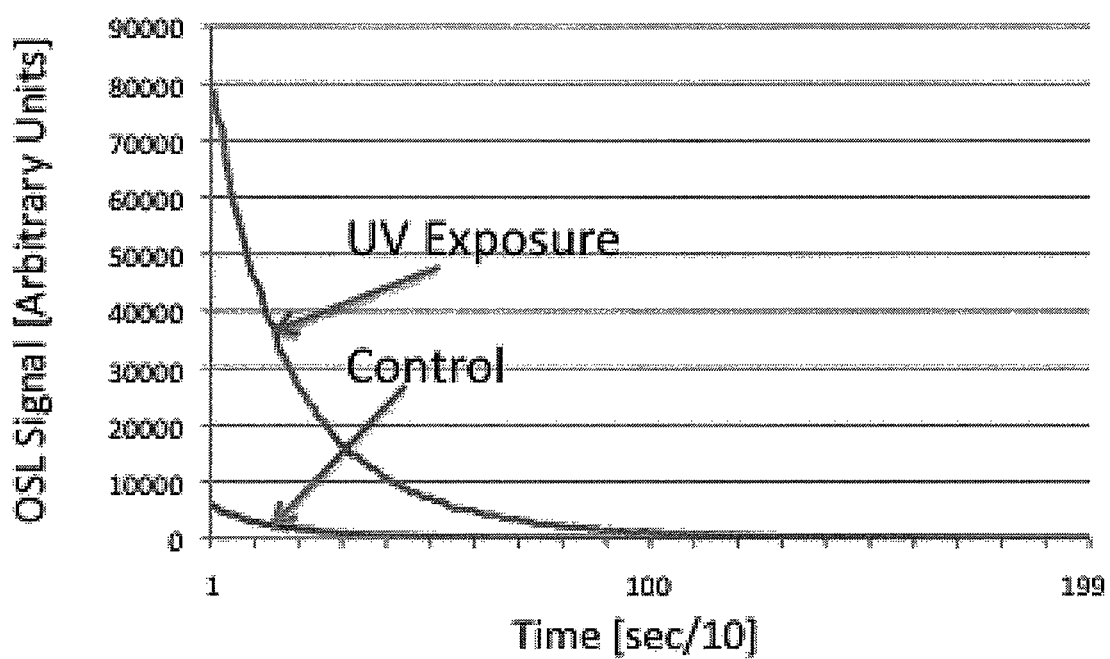
FIG. 4 shows a graph of OSL emitted light over time from irradiated fingernail parings, and a control of non-irradiated fingernail parings.

Fingernail parings were exposed to 30 minutes UV light from a standard laboratory UV source (UVB—300 nm) and then immediately read using short pulse of UV light (3 seconds). The emitted OSL signal was then accumulated for another 20 seconds as shown in FIG. 4, at ambient temperature. The controls were read in a similar way but were not exposed to the initial 30 minutes of UV light. The OSL signal of the exposed samples was at least about 20 times greater than the control.

EXAMPLE 4

A lower limit for detection using the method as in Examples 1-3 is determined by exposing fingernail parings to various types of radiation at decreasing levels of ionizing radiation. OSL signals are measured. The minimum exposure to ionizing radiation that can be detected is thus determined.

EXAMPLE 5

A calibration curve for various exposures to ionizing radiation can be determined by exposing fingernail to known doses of ionizing radiation. OSL signals are measured. A standard curve showing OSL signal correlated to dose of ionizing radiation is generated. Calibration curves can be generated for other types of radiation sources using similar methodology.

EXAMPLE 6

A calibration curve for various exposures to ionizing radiation over time is determined by exposing fingernail parings to a known dose of ionizing radiation. OSL signals are measured at various times subsequent to exposure to the ionizing radiation. A standard curve showing OSL signal correlated to dose of ionizing radiation with time is thus generated. Calibration curves can be generated for other types of radiation sources using similar methodology.

All references cited herein are incorporated herein by reference in their entirety. To the extent publications and patents or patent applications incorporated by reference contradict the disclosure contained in the specification, the specification is intended to supersede and/or take precedence over any such contradictory material.

To the extent publications and patents or patent applications incorporated by reference herein contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein.

Terms and phrases used in this application, and variations thereof, unless otherwise expressly stated, should be construed as open ended as opposed to limiting. As examples of the foregoing, the term 'including' should be read to mean 'including, without limitation' or the like; the term 'comprising' as used herein is synonymous with 'including,' 'containing,' or 'characterized by,' and is inclusive or open-ended and does not exclude additional, unrecited elements or method steps; the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise. In addition, as used in this application, the articles 'a' and 'an' should be construed as referring to one or more than one (i.e., to at least one) of the grammatical objects of the article. By way of example, 'an element' means one element or more than one element.

The presence in some instances of broadening words and phrases such as 'one or more', 'at least', 'but not limited to', or other like phrases shall not be read to mean that the narrower case is intended or required in instances where such broadening phrases may be absent.

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the invention to the specific embodiments and examples described herein, but rather to also cover all modification and alternatives coming with the true scope and spirit of the invention.

What is claimed is:

1. A method for detecting exposure of a biological material to ionizing radiation, comprising:
    exposing a biological material to ultraviolet light at an intensity, a wavelength, and a duration effective to induce luminescence in the biological material; and
    detecting light emitted from the biological material due to the induced luminescence, wherein a difference in an amount of light emitted from the biological material and light emitted from a control material that has not been exposed to ionizing radiation is indicative of exposure of the biological material to ionizing radiation, wherein the ionizing radiation is selected from the group consisting of x-rays, gamma rays, beta particles, neutrons, alpha particles, heavy ions and protons.

2. The method of claim 1, wherein the biological material comprises keratin.

3. The method of claim 2, wherein the biological material is selected from the group consisting of nail, hair, skin, carapace, claw, quill, beak, hoof, and feather.

4. The method of claim 1, wherein exposing and detecting are performed at about 15° C. to about 35° C.

5. The method of claim 1, wherein the UV light has a wavelength of from about 200 nm to about 380 nm.

6. The method of claim 1, wherein the emitted light has a wavelength of from about 380 nm to about 750 nm.

7. The method of claim 1, wherein the material is an in vivo sample.

8. The method of claim 1, wherein the material is an ex vivo sample.

9. A method for determining a radiation parameter for exposure to ionizing radiation of a biological material exposed to ionizing radiation, comprising:
    exposing a biological material to ultraviolet light effective to stimulate luminescence in the biological material;
    measuring an amount of emitted light from the material;
    comparing a value representative of the amount of emitted light with a correction factor; and
    estimating a radiation parameter for exposure to ionizing radiation of the biological material exposed to ionizing radiation based at least in part on the correction factor, wherein the ionizing radiation is selected from the group consisting of x-rays, gamma rays, beta particles, neutrons, alpha particles, heavy ions and protons.

10. The method of claim 9, wherein the radiation parameter is selected from the group consisting of a radiation cumulative dose, a radiation dose rate, an instantaneous radiation dose rate, an amount of radiation energy deposited in the material, and a rate of energy deposition in the material.

11. The method of claim 9, wherein the biological material comprises keratin.

12. The method of claim 11, wherein the biological material is selected from the group consisting of nail, hair, skin, carapace, claw, quill, beak, hoof, and feather.

13. The method of claim 9, wherein exposing and measuring are performed at about 15° C. to about 35° C.

14. The method of claim 9, wherein the UV light has a wavelength of from about 200 nm to about 380 nm.

15. The method of claim 9, wherein the emitted light has a wavelength of from about 380 nm to about 750 nm.

16. A device for detecting exposure of a biological material to ionizing radiation comprising:
    a UV light source configured to generate UV light capable of inducing luminescence in a biological sample that has been exposed to ionizing radiation;
    a detector adapted to detect light emitted from the biological sample;
    a chamber or orifice adapted to receive a biological sample; and
    a central processing unit configured to calculate a parameter for exposure to ionizing radiation, wherein the ionizing radiation is selected from the group consisting of x-rays, gamma rays, beta particles, neutrons, alpha particles, heavy ions and protons.

17. The device of claim 16, wherein the material comprises keratin.

18. The device of claim 16, further comprising a central processing unit and memory.

19. The device of claim 16, wherein the chamber is adapted for receiving an ex vivo biological sample.

20. The device of claim 16, wherein the chamber is adapted for receiving an in vivo biological sample.

21. The device of claim 16, configured to be operated at ambient temperature.

22. The device of claim 16, which is portable and/or handheld.

23. The device of claim 16, wherein the UV light has a peak emission wavelength of about 300 nm or of about 254 nm.

24. The device of claim 16, wherein the detector is adapted to detect light emitted from the biological sample for a period of about 20 seconds.

* * * * *